United States Patent
Mühmel et al.

[11] Patent Number: 6,135,431
[45] Date of Patent: Oct. 24, 2000

[54] SCENT CARTRIDGE

[75] Inventors: Gerhold Mühmel, Hamberge; Mark Griesbach, Bad Schwartau; Rita Hamann, Lübeck, all of Germany

[73] Assignee: Dräger Sicherheitstechnik GmbH, Germany

[21] Appl. No.: 09/205,270

[22] Filed: Dec. 4, 1998

[30] Foreign Application Priority Data

Dec. 5, 1997 [DE] Germany .................. 197 53 956

[51] Int. Cl.[7] .................................................. B01F 3/04
[52] U.S. Cl. ............................. 261/101; 261/DIG. 17; 96/149; 96/153; 239/53; 239/55; 422/123
[58] Field of Search .......................... 261/104, 101, 261/DIG. 17, DIG. 65; 96/222, 149, 153; 239/53, 54, 55, 56; 422/123, 124

[56] References Cited

U.S. PATENT DOCUMENTS

| | | |
|---|---|---|
| 2,578,827 | 12/1951 | Munnecke . |
| 3,552,591 | 1/1971 | Wimmer ................... 215/37 |
| 4,146,566 | 3/1979 | Gaiser . |
| 4,346,840 | 8/1982 | Gaiser et al. .............. 239/55 |
| 4,617,157 | 10/1986 | Stein et al. . |
| 4,830,643 | 5/1989 | Sassa et al. ............... 55/522 |
| 5,115,975 | 5/1992 | Shilling . |
| 5,500,038 | 3/1996 | Dauber et al. ............. 96/135 |

FOREIGN PATENT DOCUMENTS

| | | | |
|---|---|---|---|
| 468331 | 9/1950 | Canada ..................... | 239/55 |
| 40 33 076 C2 | 2/1993 | Germany . | |
| 42 35 624 C1 | 7/1993 | Germany . | |
| 40 33 079 C2 | 2/1994 | Germany . | |
| 44 17 739 C1 | 6/1995 | Germany . | |
| 51-118837 | 10/1976 | Japan . | |
| 53-29943 | 3/1978 | Japan . | |
| 1-144727 | 10/1989 | Japan . | |
| 4-106329 | 4/1992 | Japan . | |
| 1286051 | 8/1972 | United Kingdom . | |

OTHER PUBLICATIONS

JP C-790 vol. 14 No. 571, May 10, 1990, Japan.

*Primary Examiner*—David A. Simmons
*Assistant Examiner*—Robert A. Hopkins
*Attorney, Agent, or Firm*—McGlew & Tuttle, P.C.

[57] ABSTRACT

A scent cartridge (1) with a substrate (3), wherein the latter consists of porous particles of silica gel, activated carbon and/or aluminum oxide, which are impregnated with scents or active ingredients. The substrate (3) is fixed in a small cylindrical glass or aluminum tube (2) by means of wire-mesh caps (4) made of metal or plastic. A membrane disk (6) is sealingly held on each flanged edge (5) of the small glass or aluminum tube (2) by means of a cap (7) each so that the membrane disks (6) can be punctured with needles or cannulae for releasing scents or active ingredients and an air or carrier gas flow controlled in a time-dependent manner is then admitted to the scent cartridge (1).

20 Claims, 1 Drawing Sheet

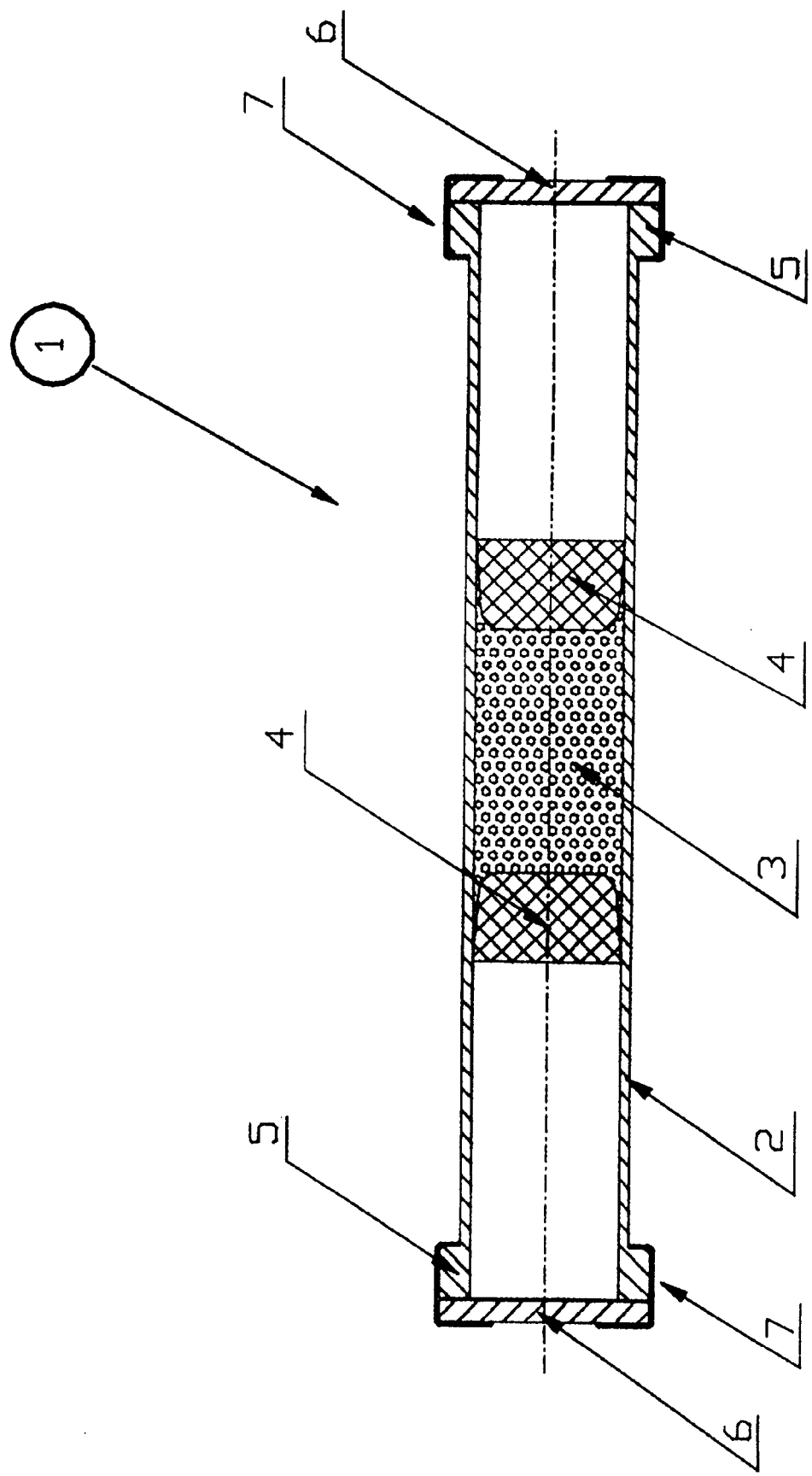

SCENT CARTRIDGE

FIELD OF THE INVENTION

The present invention pertains to a scent cartridge with a substrate for receiving scents or active ingredients.

BACKGROUND OF THE INVENTION

Such scent cartridges are described, e.g., in DE 44 17 739 C1. A scent dispenser consisting of a porous sintered glass for the storage and the controlled release of evaporable substances is described in that publication. These prior-art scent dispensers shall release scents or active ingredients into the environment over a prolonged period of several weeks to months as uniformly as possible, at a constant concentration and with unchanged composition.

Various possibilities of releasing larger or smaller amounts of scents/active ingredients from a storage means in a controlled manner have become known from German Patents Nos. 40 33 076 C2, DE 40 33 079 C2, and DE 42 35 624 C1. Larger or smaller amounts of air or carrier gas are now passed in a time-dependent manner through one or more scent/active ingredient-containing storage means as a function of the time-dependent control signals of a receiver, a computer or an electronic or optical memory, so that the consumer, viewer or even the listener of a movie, video or piece of music, computer program or a real presentation, e.g., of an edible consumer product, can perceive corresponding odor impressions characteristic of the particular product, suited to the visual/acoustic impressions.

SUMMARY AND OBJECTS OF THE INVENTION

The primary object of the present invention is to propose a compact, inexpensive scent/active ingredient cartridge of a simple design, which can also be manufactured automatically in large lots, which is suitable, in particular, for the specific and reproducible release of scents/active ingredients, which takes place by means of an air or carrier gas flow controlled in a time-dependent manner.

According to the invention, a scent cartridge is provided with a substrate for taking up scents or active ingredients. The substrate includes porous particles of silica gel, aluminum oxide and/or activated carbon, which are impregnated with scents or active ingredients and are arranged in a sealed and gas-filled volume of about 1 to 30 cm$^3$, through which gas can flow.

According to another aspect of the invention, a process is provided including providing a scent cartridge with a substrate for taking up scents or active ingredients in which the substrate includes porous particles of silica gel, aluminum oxide and/or activated carbon, which are impregnated with scents or active ingredients and are arranged in a sealed and gas-filled volume of about 1 to 30 cm$^3$. A time-dependently controlled volume flow of a carrier gas is provided flowing through the scent cartridge. The cartridge is used as a source of scent for the controlled release of scents taken up in the substrate.

One essential advantage of the present invention is that an inexpensive, easy-to-manufacture, but highly effective scent cartridge, which is especially suitable for the release of scents/active ingredients to a carrier gas flow passed through the scent cartridge in a time-dependently controlled manner, is made available with simple components. The scent cartridges according to the present invention have the following design: Generally spherical or irregularly broken, wide-pored particles, which essentially consist of silica gel, activated carbon and/or aluminum oxide and are impregnated with scents or active ingredients, are positioned as a porous substrate in a small cylindrical tube made of glass or especially aluminum, whose surface is anodically oxidized. Good scent release properties were obtained with about 1 g of substrate per scent cartridge for a carrier gas volume flow rate of about 8 L per minute with a flow time of 15 sec, which was repeated up to 1,000 times, and the substrate was impregnated with about 0.5 to a maximum of 1.1 g of scents/active ingredients. The substrate particles had a mean diameter of about 1.0 to 1.8 mm and especially 1.2 to 1.6 mm and a porosity, expressed as the specific pore volume, of 0.6–1.8 mL/g of substrate pore volume percentage to total particle volume. The substrate particles used are preferably wide-pored in order to make possible the impregnation or loading with scents or active ingredients. If the particle size becomes too small, there is a risk of entrainment by the carrier gas flow; in addition, the flow resistance of the substrate packing may become undesirably high. If the particles are too large, the ease of handling of the filling of the cartridges or even the ability to be impregnated with the scents/active ingredients or the ability to release same may become poorer. The small cylindrical tube is filled with air, nitrogen, carbon dioxide or a noble gas, depending on the sensitivity of the scents/active ingredients used and is closed gas-tightly on both sides with a flexible membrane disk, which is impermeable to gas. Thus, the scent cartridges may be stored over several weeks before they are put into operation, optionally in a cooled and dark place, in order to prevent undesired changes from occurring in the sometimes highly sensitive scents/active ingredients.

The impregnating scents/active ingredients are released by passing optionally heated air or another, especially inert carrier gas, e.g., nitrogen or a noble gas through openings in the membrane disks in a controlled manner, e.g., after puncturing on both sides with needles or cannulae, so that a controlled discharge of the scents from the scent cartridge is possible through small openings. The porous particles forming the substrate are preferably used in the washed state. Especially good results were obtained with scent/active ingredient loads of about 0.7 to 1.1 g of scent per g of silica gel, 0.6 to 1.0 g of scent per g of $Al_2O_3$ and of 0.5 to 0.9 g of scent per g of activated carbon. The impregnation is performed in practice in a glass or stainless steel container, as a result of which the aromatic substances or perfume oils do not undergo any changes and good cleaning is possible. The scents/active ingredients are intimately mixed with the substrate particles in the process. The filling of the impregnated substrate material into the scent cartridges according to the present invention may be performed, as a rule, without a protective gas. An inert protective gas atmosphere consisting of nitrogen, carbon dioxide or a noble gas may also be advantageous in the case of especially sensitive scents/active ingredients, which are, in addition, to be stored over rather long periods of time.

One exemplary embodiment will be explained below on the basis of the drawing with the only FIGURE.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

In the drawing:

The FIGURE is a sectional view of a scent cartridge according to the present invention.

DESCRIPTION OF THE PREFERRED EMBODIMENT

Referring to the drawing in particular, a substrate 3 is impregnated with scents/active ingredients in an amount of about 1.5 to 2.1 g. The substrate 3 has a mean particle diameter of about 1.0 to 1.8 mm and has a porosity of 0.6–1.8 mL/g of silica gel, activated carbon and/or aluminum oxide ($Al_2O_3$), expressed as the specific pore volume. The substrate 3 is disposed in the middle area of a housing which is a small cylindrical glass or aluminum tube 2 having a length of about 20 to 120 mm and an internal diameter of 10 to 20 mm. The substrate 3 essentially consists of spherical, broken or extruded, porous particles including silica gel, activated carbon and/or aluminum oxide ($Al_2O_3$). In the FIGURE, the substrate 3 is held by gas-permeable wiremesh caps 4 made of metal or plastic. Both openings of the small glass or aluminum tube 2 are provided with a flanged edge 5. A membrane disk 6, which consists of a material that is possibly inert for the scents and is impermeable to gases, e.g., silicone rubber or plastic, optionally with an additional inert coating, is located on each flanged edge 5. The membrane disks 6 are held sealingly at the flanged edge 5 with a cap 7 each, preferably one made of aluminum or another metal, with an opening diameter of about 6 to 10 mm.

The material of the membrane disk is selected depending on the properties of the scents to be preserved. Teflon-coated membrane disks 6 or ones consisting purely of butyl rubber are preferably used for scents containing aldehyde or ketone components. Scents containing saturated, unsaturated or aromatic components may be sealed with membrane disks 6 coated with Viton. The membrane disks 6 have a thickness of 0.5 to 2 mm. For opening, the scent cartridges 1 are punctured with corresponding needles or cannulae, while the soft material of the membrane disk closes sealingly around the needles or cannulae. On the one hand, the scent cartridges 1 according to the present invention are closed before their use such that the discharge of the scents or the entry of substances, especially gases, which are detrimental to the scent, from the environment are prevented from occurring, and adaptation of the scent cartridge 1 to a time-controlled scenting system is possible, on the other hand, due to a simple mechanism. The scents with the substrate 3 may also be sealed and stored under an inert gas atmosphere, e.g., one consisting of nitrogen, carbon dioxide or argon.

A time-controlled carrier gas flow is passed through the scent cartridge 1 for release to the environment. The carrier gas is optionally temperature-controlled, so that a larger amount of scents or active ingredients are released from the substrate 3 and are taken up by the carrier gas at higher temperature at a given carrier gas volume flow. In the practical application in the scenting system, six scent cartridges 1 according to the present invention are used in one packaging unit, and the six scent cartridges are impregnated differently and a carrier gas flow flows through them individually in a time-controlled manner after insertion into the scenting system and opening of the membrane disks 6. The carrier gas flow is passed by valves through every individual scent cartridge 1 at a volume flow rate of about 8 L per minute during a period of about 15 sec per demonstration. Air or carrier gas may thus pass through a scent cartridge 1 up to a thousand times without the amount of scents or active ingredients released per flowthrough decreasing markedly.

The scents or active ingredients contain one or more substances from the group of the essential oils, natural aromatic substances, aromatic substances identical to natural aromatic substances, or other synthetic aromatic substances.

While a specific embodiment of the invention has been shown and described in detail to illustrate the application of the principles of the invention, it will be understood that the invention may be embodied otherwise without departing from such principles.

What is claimed is:

1. A scent cartridge, comprising:
   a substrate for taking up scents, said substrate including porous particles of silica get, aluminum oxide and/or activated carbon, said porous particles having a diameter of about 1.0 to 1.8 mm and a porosity of 0.6–1.8 mL/g, expressed as specific pore volume;
   scents impregnating said substrate;
   a housing defining a gas-tightly sealed and gas-filled volume of about 1 to 30 $cm^3$, said housing having ends which are openable and through which gas can flow.

2. The scent cartridge in accordance with claim 1, wherein said substrate includes spherical or irregularly broken particles of silica gel with a porosity of 0.8–1.8 mL/g of silica gel, expressed as specific pore volume.

3. The scent cartridge in accordance with claim 1, wherein said substrate includes spherical, irregularly broken or extruded particles of activated carbon with a porosity of 0.7–1.2 mL/g of activated carbon, expressed as specific pore volume.

4. The scent cartridge in accordance with claim 1, wherein said substrate includes spherical or irregularly broken particles of aluminum oxide ($Al_2O_3$) with a porosity of 0.6–1.2 mL/g of aluminum oxide ($Al_2O_3$), expressed as specific pore volume.

5. The scent cartridge in accordance with claim 1, wherein substantially 1 g of said substrate is included in the scent cartridge, wherein said scents include one or more substances from the group of the essential oils, natural aromatic substances, aromatic substances identical to natural aromatic substances, or other synthetic aromatic substances.

6. The scent cartridge in accordance with claim 1, wherein said housing is one of a small glass or aluminum tube of a substantially round cross section with an internal diameter of 10–20 mm and a length of 20–120 mm, said housing including said substrate and said scents in an interior space and being closed at both ends respectively with a gas-impermeable membrane disk.

7. The scent cartridge in accordance with claim 1, further comprising two metallic wiremesh caps, wherein said substrate is fixed in a gas-permeable manner centrally in said housing by said two metallic wiremesh caps.

8. The scent cartridge in accordance with claim 1, wherein said gas in said gas filled volume is air or one or more gases from the group comprising nitrogen, carbon dioxide or a noble gas.

9. A scent cartridge, comprising:
   a substrate for taking up scents, said substrate including porous particles of silica gel, aluminum oxide and/or activated carbon;
   scents impregnating said substrate;
   a housing defining a gas-tightly sealed and gas-filled volume of about 1 to 30 $cm^3$, said housing including said substrate and said scents in an interior space and being closed at both ends respectively with a gas-impermeable membrane disk being openable and through which gas can flow.

10. The scent cartridge in accordance with claim 9, wherein each said membrane disk is held in a gas-sealing manner by means of a metallic cap with a round opening diameter of preferably 6 to 10 mm.

11. The scent cartridge in accordance with claim 9, wherein each said membrane disk has a thickness of about 0.5 to 2 mm and essentially consist of one of a rubber or plastic or silicone or butyl rubber, or fluoroelastomer.

12. The scent cartridge in accordance with claim 9, wherein said membrane disks are coated on one side or on both sides with an additional inert, gas-impermeable barrier material.

13. The scent cartridge in accordance with claim 12, wherein said gas-impermeable barrier material is aluminum foil or Teflon.

14. A process comprising the steps of:
providing a substrate for taking up scents, said substrate including porous particles of silica gel, aluminum oxide and/or activated carbon;
impregnating the substrate with scents or active ingredients;
disposing said substrate impregnated with said scents or active ingredients in a housing defining a gas-tightly sealed and gas-filled volume of about 1 to 30 $cm^3$, said housing having first and second ends;
puncturing said first and second ends of said housing with a needle for allowing a gas flow through said housing;
providing a time-dependently controlled volume flow of a carrier gas through said housing to provide a source of scent for a controlled release of scents taken up in said substrate.

15. The process in accordance with claim 14, further comprising using a carrier gas that essentially consists of air, nitrogen, helium and/or argon.

16. The process in accordance with claim 14, further comprising controlling the amount of scents released into the carrier gas by varying a temperature of said carrier gas and/or varying a volume of carrier gas flowing through the housing.

17. A scent cartridge, comprising:
a housing defining a gas-filled volume of approximately 1 to 30 $cm^3$, said housing being closed to block passage of gas through said housing, said housing having first and second ends each including a membrane, said each membrane being puncturable by a needle and formed of a material sealingly closeable around an inserted needle;
a substrate arranged in said housing for taking up and releasing scents, said substrate including porous particles of silica gel, aluminum oxide and/or activated carbon,
a scent impregnated into said substrate.

18. The scent cartridge in accordance with claim 17, wherein:
one of said membranes is puncturable by a needle to form a inlet for a gas flow through said housing and said substrate, another of said membranes is positioned on an opposite side of said housing and is puncturable by another needle to form an outlet for the gas flow.

19. The scent cartridge in accordance with claim 18, wherein:
said housing is a tube with an internal diameter of 10–20 mm and a length of 20–120 mm;
said substrate is formed with spherical or irregularly broken particles having a diameter of about 1.0 to 1.8 mm and a porosity of 0.6–1.8 mL/g expressed as specific pore volume.

20. The scent cartridge in accordance with claim 19, wherein:
substantially 1 g of said substrate is included in the scent cartridge;
said scent includes one or more substances from a group of essential oils, natural aromatic substances, aromatic substances identical to natural aromatic substances, or other synthetic aromatic substances.

* * * * *